| United States Patent [19] | [11] Patent Number: 4,560,774 |
| Pettit et al. | [45] Date of Patent: Dec. 24, 1985 |

[54] MACROCYCLIC LACTONES

[75] Inventors: George R. Pettit, Paradise Valley; Cherry L. Herald, Tempe, both of Ariz.

[73] Assignee: Arizona State University, Tempe, Ariz.

[21] Appl. No.: 513,148

[22] Filed: Jul. 12, 1983

Related U.S. Application Data

[63] Continuation-in-part of Ser. No. 442,487, Nov. 17, 1982, abandoned.

[51] Int. Cl.[4] ............................................ C07D 493/22
[52] U.S. Cl. .................................... 549/267; 514/450
[58] Field of Search ........................ 549/267; 424/279

[56]  References Cited

PUBLICATIONS

G. G. Villela, Proc. Soc. Exptl. Biol. Med., 68, 531–533, (1948).
J. S. Carlé, et al., J. Org. Chem., 45, 1586–1589, (1980).
J. S. Carlé, et al., J. Org. Chem., 46, 3440–3443, (1981).
Y. Okami, et al., J. Antibiot., 29, 1019–1025, (1976).
H. Nakamura, et al., J. Antibiot., 30, No. 9, 714–719, (1977).
G. R. Pettit, et al., Nature, 227, 962–963, (1970).

*Primary Examiner*—Jane T. Fan
*Attorney, Agent, or Firm*—Kenneth A. Weber

[57]  ABSTRACT

New and exceptionally potent antineoplastic agents designated bryostatin 1, bryostatin 2 and bryostatin 3 have been isolated from the marine animal *Bugula neritina* L. (Bryozoan phylum). An x-ray crystallographic analysis led to the assignment of novel structures shown in Charts I, II and III.

3 Claims, No Drawings

MACROCYCLIC LACTONES

DESCRIPTION

CROSS REFERENCE TO RELATION APPLICATION

This is a continuation-in-part of our pending application Ser. No. 442,487 filed on Nov. 17, 1982, now abandoned.

BACKGROUND OF THE INVENTION

The only prior chemical investigations of bryozoa appear to be (1) our initial report that certain bryozoa such as *Bugula neritina* contain anticancer constituents (Pettit, G. R.; J. F. Day, J. L. Hartwell, H. B. Wood, *Nature,* 1970, 227: 962-963); (2) a preliminary study of an adrenochrome-like pigment in the same species (Villela, G. G. *Proc. Soc. Exptl. Biol. Med.* 1948, 68: 531-553); and (3) isolation of the indoles flustramines A and B from *Flustra foliacea* (Carle', J. S.; Christopherson, C., *J. Org. Chem.* 1980, 45: 1586-1589; Carle', J. S.; Christopherson, C., *J. Org. Chem.* 1981, 46: 3440-3448). Of the presently known cyclic ionophores, only the *Streptomyces griseus* component aplasmomycin seems distantly related to bryostatin 1. (Okami, Y.; Okazaki, T.; Kitahara, T.; Umezawa, H.; *J. Antibiot.* 1976, 29: 1019; and Nakamura, H.; Iitaka, Y.; Kitahaa, T.; Okazaki, T.; Okami, Y., *J. Antibiot.* 1977, 3.0: 714).

Financial assistance was provided by Contract N01-CM-97262 with the Division of Cancer Treatment, NCI, National Institutes of Health, DHW, Grant Nos. CA16049-01 through 07 awarded by the National Cancer Institute, DHW, Mrs. Mary Dell Pritzlaff, the Olin Foundation (Spencer T. and Ann W.), the Fannie E. Rippel Foundation, Mrs. Eleanor W. Libby, the David Ware Waddell Foundation, Mrs. Pearl Spear, and Mr. Robert B. Dalton. For other very helpful assistance we are pleased to thank Drs. J. D. Douros, J. J. Einck, D. Gust, R. R. Inners, L. W. Knapp, P. Lohavanijaya, M. I. Suffness, J. M. Schmidt, J. Witschel, Jr., Mr. M. A. Carlson, Miss B. L. Norfleet, Miss K. M. Welch, the Smithsonian Institution Oceanographic Sorting Center, and the National Science Foundation Regional Facility at the University of South Carolina (CH78-18723). We also acknowledge support provided by NIH CA24487 (JC), and the National Science Foundation.

BRIEF SUMMARY OF THE INVENTION

Novel, highly active, macrocyclic lactone antitumor antibiotics, bryostatin 1, bryostatin 2, and bryostatin 3, were isolated from *Bugula neritina,* a marine bryozoan. Bryostatin 1 increases the lifespan of tumor-bearing mice by 52-96 percent at an injected dose of only 10-70)g/kg. Bryostatin 2 and 3 increase the lifespan of tumor-bearing mice by about 60 percent at an injected dose of 30 μg/kg. The structural formula for bryostatin 1 is shown in Chart I, that for bryostatin 2 in Chart II, and that for bryostatin 3 in Chart III.

DETAILED DESCRIPTION OF THE INVENTION

Description of the Organism

Marine animals of the phylum Ectoprocta (usually termed Bryozoa or Polyzoa) are colonial filter-feeders and each member (polypide) is enclosed in a separate unit (zooecium). Because of their superficial appearance Bryozoa are commonly known as sea-mats and false corals.

*Bugula neritina* (Linnaeus) is a widely distributed moss-like bryozoan and is well known for its ability to attach to ship hulls. One type of *Bugula neritina* polypide (an avicularium) resembles the beak of a bird and by closing one jaw against the other is able to protect the colony from uninvited encroachment. Such avicularia are a common component of *B. neritina.*

*B. neritina* and other marine bryozoans are described by J. H. Day in "A Guide to Marine Life on South African Shores," Balkema. A. A., Cape Town, 1974, p. 123; and by P. H. Benson and R. W. Moncreiff in "The Effects of Zinc and pH on Larval Attachment of the Common Fouling Organism, *Bugula neritina*"; Compt. Rend. du Contres. International de la Corrosion Marine et de Salissures. 4th Antibes and Juan-le-Pins, Fr., July 14-18, 1976.

Location of the Organism

The large quantities of bryostatins 1 and 2 required for structure determination were isolated from 500 kg of *Bugula neritina* specimens that were collected from Monterrey Bay, Calif. (36° N. latitude, 122° W. longitude). They were collected at low tidal depths of 0-5 ft. Other locations where these organisms have been collected include Tokyo Bay, Japan (35° N., 140° E.) and sites near Sinaloa, Mexico and Alligator Harbor, Fla. Extracts of *B. neritina* from three separate collections all contained antineoplastic activity.

Isolation and Purification of Bryostatins

A variety of methods can be used to isolate and purify the bryostatins from samples of *B. neritina,* including solvent extraction, partition chromatography, silica gel chromatography, liquid-liquid distribution in a Craig apparatus, adsorption on resins, and crystallization from solvents.

The isolation and purification methods chosen can be monitored at each step by performing in-vitro and/or in-vivo antitumor tests as described by R. I. Geran, N. H. Greenberg, M. M. MacDonald, A. M. Schumacher and B. S. Abbot in *Cancer Chemother. Rep.* Part 3, Vol. 3 (2): 1-103 (1972); and by Schmidt, J. M.; Pettit, G. R. in *Experientia* 1978, 34: 659-660. Such tests include the determination of the concentration of active material required to inhibit the growth of tumor cells in culture, (e.g. the concentration required to inhibit growth by 50 percent or the $E.D._{50}$) and of the dose of active material required to prolong the life of mice bearing transplanted tumors.

The following examples describe preferred processes, but are not to be construed as limiting.

EXAMPLE 1

Extraction and Solvent Partitioning

Five hundred kg wet weight of the marine animals were immersed in 2-propanol immediately after collecting and were shipped to the processing site in that condition. The shipping solution (150 gallons) was drained from the animals and concentrated to an aqueous slurry using a Buchi R-150 E evaporator at 50° C. This concentrate was divided into portions and repeatedly extracted with methylene chloride (5 to 6 times). The combined, dried methylene chloride extracts from the shipping solution weighed 511.0 g and was toxic to mice at an injected dose of 3.75 mg/kg.

After draining off the shipping solution, the marine animals were chopped up and further extracted with a mixture of methylene chloride and methanol (1:1) for two weeks at ambient temperature. The resulting solution was drained from the animals and one part of water to four parts of solution was added to produce phase separation. The lower phase (mostly methylene chloride) was removed and evaporated to dryness using reduced pressure at 40°–45° C. To the remaining upper phase was added sufficient methylene chloride and methanol to produce a single phase (a ratio of 4:2:1 of upper phase:methylene chloride:methanol, respectively) and this solution was returned to the animal material for a second extraction at ambient temperature for 12 days. The solution resulting from the 2nd extraction was drained from the animals and water was again added to produce phase separation. The lower phase was separated and evaporated to dryness. A total of 366.1 g of dried methylene chloride extract was obtained from the two methylene chloride-methanol extractions of the animals.

The dried methylene chloride extracts (derived from the shipping solution and from extraction of the chopped animals) were further separated by taking small portions and subjecting each to solvent partitioning beginning with methanol:water (9:1)/hexane (4 times). The dried hexane extracts were inactive in P 388 mouse tumor tests. The aqueous methanol layers were further diluted with water to a ratio of 8:2 and were extracted repeatedly with carbon tetrachloride (9 times). The carbon tetrachloride extracts were dried and assayed for antitumor activity. The 149.6 g portion derived from the shipping solution was toxic to mice at a dose of 1.5 mg/kg while the 64.3 g amount derived from the methylene chloride-methanol extraction of the chopped animals was active in a PS mouse tumor test system, producing a 46% increase in lifespan at a dose of 10 mg/kg.

The entire extraction and solvent partitioning process described above is shown in schematic form in Chart IV.

EXAMPLE 2

Chromatographic Purification

The dried carbon tetrachloride extracts were further purified by two preparative chromatography procedures in large glass columns (Glenco, 9.5×112 cm) containing Sephadex LH-20 (Pharmacia, Fine Chemicals) equilibrated with the eluting solvent mixture. A Gilson FC-220 was used to collect fractions of the eluate and a thin layer chromatographic (TLC) system was used to monitor the eluate fractions for solutes. The TLC system consisted of Analtech silica gel GHLF Uniplates developed with a methylene chloride:methanol (95:5) solvent system. Separated components were visualized by spraying with an anisaldehyde acetic acid-sulfuric acid solution (E. Stahl, "Thin Layer Chromatography," Academic Press, New York, 1971, p. 485). Fractions corresponding to "peaks" of eluted solutes were pooled, dried, and checked for antitumor activity in a transplanted mouse tumor system (PS).

The first chromatographic separation procedure was performed with a solvent system of methylene chloride:methanol (1:1). Combined fractions which produced an increase in lifespan of at least 35% (PS system) were used for the second chromatographic separation. The total amount of bioactive material was 122.8 g.

The second chromatographic separation procedure was performed with a solvent system of hexane:toluene:methanol (3:1:1). A total of five columns were required to process the bioactive material from the first chromatographic separation procedure. One of these columns was used to process 33.9 g of bioactive material into 780 fractions of 19 ml each. After evaporation at room temperature, fractions 353–375 yielded a total of 120 mg of colorless crystals. Recrystallization of this material from methylene chloride-methanol yielded 91 mg of crystals that gave a single spot on TLC at Rf 0.7 and had an uncorrected melting point of 230°–235° C. (Koefler melting point apparatus). This material was designated bryostatin 1.

Another column was used to process 14.8 g of bioactive material into 459 fractions of 19 ml each. Fractions 385–400 yielded a total of 83.4 mg of crystalline residue. Recrystallization of this material from methylene chloride-methanol-water yielded 7.5 mg of colorless crystals that gave a single spot on TLC at Rf 0.54. (This TLC was developed with a 90:10 methylene chloride:methanol solvent system) and had an uncorrected melting point of 201°–203° C. This material was designated bryostatin 2.

An additional 42 mg of bryostatin 2 was recovered from 75 mg of the above mother liquor residue by silica gel chromatography on three Merck (Darmstadt) Size A (40–63 μm) prepack columns used in series. The columns were eluted with gradients of methylene chloride in methanol starting with neat methylene chloride and ending with a 90:10 mixture of methylene chloride:methanol.

Another fraction (168.5 mg) enriched in bryostatin 2 was further chromatographed on silica gel prepack columns (three Merck Size B in series). A solvent gradient starting with methylene chloride then adding increments of methanol to a final ratio of 85:15 methylene chloride:methanol was used. A total of 287 fractions, 5 ml each, were collected. Bryostatin 3 was contained in fractions 130-5 (72.2 mg).

Bryostatin 3 required further purification using the same gradient but smaller columns (three Merck Size A in series). Pure bryostatin 3 was eluted with the gradient 99:1 to 97:3 methylene chloride:methanol in fractions 92-8 (42.3 mg), with 144 total fractions taken. This material was an amorphous solid; attempts at crystallization resulted in decomposition.

EXAMPLE 3

Derivatives of the bryostatins

The bryostatins have free hydroxyl and replaceable acyl groups (see Charts I, II and III). Thus, various acyl esters of these compounds can be prepared by methods well known to those skilled in the art. Acyl derivatives of the byostatins can be used for the same biological purposes as the parent conpunds.

Acids which can be used in the acylation of bryostatins include:

(a) saturated or unsaturated, straight or branched chain aliphatic carboxylic acids, for example, acetic, propionic, butyric, isobutyric, tert-butylacetic, valeric, isovaleric, caproic, caprylic, decanoic, dodecanoic, lauric, tridecanoic, myristic, pentadecanoic, palmitic, margaric, stearic, acrylic, crotonic, undecylenic, oleic, hexynoic, heptynoic, octynoic acids, and the like; (b) saturated or unsaturated, alicyclic carboxylic acids, for example, cyclobutanecarboxylic acid, cyclopentanecarboxylic acid, cyclopentenecarboxylic acid, methylcyclopentenecarboxylic acid, cyclohexanecarboxylic acid, dimethylcyclohexanecarboxylic acid, dipropylcyclohexanecarboxylic acid, and the like; (c) saturated or unsaturated, alicyclic aliphatic carboxylic acids, for example, cyclopentaneacetic acid, cyclopentanepropionic acid, cyclohexaneacetic acid, cyclohexanebutyric acid, methylcyclohexaneacetic acid, and the like; (d) aromatic carboxylic acids, for example, benzoic acid, toluic acid, naphthoic acid, ethylbenzoic acid, isobutylbenzoic acid, methylbutylbenzoic acid, and the like; and (e) aromatic-aliphatic carboxylic acids, for example, phenylacetic acid, phenylpropionic acid, phenylvaleric acid, cinnamic acid, phenylpropiolic acid and naphthylacetic acid, and the like. Suitable halo-, nitro-, hydroxy-, keto-, amino-, cyano-, thiocyano-, and lower alkoxyhydrocarbon carboxylic acids include hydrocarboncarboxylic acids as given above which are substituted by one or more of halogen, nitro, hydroxy, keto, amino, cyano, or thiocyano, or loweralkoxy, advantageously loweralkoxy of not more than six carbon atoms, for example, methoxy, ethoxy, propoxy, butoxy, amyloxy, hexyloxy, and isomeric forms thereof. Examples of such substituted hydrocarbon carboxylic acids are:

mono-, di-, and trichloroacetic acid;
α- and β-chloropropionic acid;
α- and γ-bromobutyric acid;
α- and δ-iodovaleric acid;
mevalonic acid;
2- and 4-chlorocyclohexanecarboxylic acid;
shikimic acid;
2-nitro-1-methyl-cyclobutanecarboxylic acid;
1,2,3,4,5,6-hexachlorocyclohexanecarboxylic acid;
3-bromo-2-methylcyclohexanecarboxylic acid;
4- and 5-bromo-2-methylcyclohexanecarboxylic acid;
5- and 6-bromo-2-methylcyclohexanecarboxylic acid;
2,3-dibromo-2-methylcyclohexanecarboxylic acid;
2,5-dibromo-2-methylcyclohexanecarboxylic acid;
4,5-dibromo-2-methylcyclohexanecarboxylic acid;
5,6-dibromo-2-methylcyclohexanecarboxylic acid;
3-bromo-3-methylcyclohexanecarboxylic acid;
6-bromo-3-methylcyclohexanecarboxylic acid;
1,6-dibromo-3-methylcyclohexanecarboxylic acid;
2-bromo-4-methylcyclohexanecarboxylic acid;
1,2-dibromo-4-methylcyclohexanecarboxylic acid;
3-bromo-2,2,3-trimethylcyclopentanecarboxylic acid;
1-bromo-3,5-dimethylcyclohexanecarboxylic acid;
homogentisic acid, o-, m-, and p-chlorobenzoic acid;
anisic acid;
salicylic acid;
p-hydroxybenzoic acid;
β-resorcylic acid;
gallic acid;
veratric acid;
trimethoxybenzoic acid;
trimethoxycinnamic acid;
4,4'-dichlorobenzilic acid;
o-, m-, and p-nitrobenzoic acid;
cyanoacetic acid;
3,4- and 3,5-dinitrobenzoic acid;
2,4,6-trinitrobenzoic acid;
thiocyanoacetic acid;
cyanopropionic acid;
lactic acid;
ethoxyformic acid (ethyl hydrogen carbonate);
malic acid;
citric acid;
isocitric acid;
6-methylsalicylic acid;
mandelic acid;
levulinic acid;
pyruvic acid;
glycine;
alamine;
valine;
isoleucine;
leucine;
phenylalanine;
proline;
serine;
threonine;
tyrosine;
hydroxyproline;
ornithine;
lysine;
arginine;
histidine;
hydroxylysine;
phenylglycine;
p-aminobenzoic acid;
m-aminobenzoic acid;
anthranilic acid;
aspartic acid;
glutamic acid;
aminoadipic acid;
glutamine;
asparagine;
and the like.

Physical Data for the Bryostatins

All solvents employed for chromatography were redistilled. Precoated Analtech Uniplates designated silica gel GHLF were used for TLC and spots were visualized with an anisaldehydeacetic acid-sulfuric acid spray (E. Stahl, "Thin Layer Chromatography," Academic Press, New York, 1971, p. 485). All melting points are uncorrected and were obtained using a Koefler melting point apparatus. The $^{13}$C NMR spectrum was obtained with a Bruker WH-90 NMR spectrometer (at 22.6 MHz in ppm downfield from TMS). The $^1$H NMR spectra (400 MHz) were obtained with a WH-400 NMR spectrometer. Mass spectra were determined with a Varian MAT-312 mass spectrometer. Optical rotations were measured using a Perkin-Elmer model 241 polarimeter. Ultraviolet spectra were recorded using a Hewlett-Packard 8450A UV/VIS spectrometer.

Bryostatin 1

Appearance—Colorless crystalline solid from methylene chloridemethanol.

Melting Point—230°–235° C., uncorrected.

| Thin Layer Chromatography Solvent System | Rf |
|---|---|
| CH$_2$Cl$_2$:MeOH (9:1) | 0.7 |

Ultraviolet Spectrum: Λ max (MeOH)=233 nm (ε 25,230) and 263 nm (ε 28,170).

Optical Rotation: $[\alpha]_D{}^{25°}$ C. of a 4.4% solution in methanol is +34.1°.

Electron Impact Mass Spectrum (EIMS): m/z 886 (M-H$_2$O, C$_{47}$H$_{66}$O$_{16}$), exact mass 886.4376 amu (calcd. 886.4351 for C$_{47}$H$_{66}$O$_{16}$).

Fast Atom Bombardment Mass Spectrum (FABMS): m/z 904 (M).

Infrared Spectrum (KBr): Peaks are seen at: 3740, 3400, 2970, 2950, 1735, 1716 (strongest band), 1700, 1600, 1640, 1435, 1385, 1365, 1245, 1160, 1100, 1080 and 1000 cm$^{-1}$.

$^{13}$C NMR—(22.6 MHz broad band decoupled, CDCl$_3$): δ 172.2 (s), 171.1 (s), 167.0 (s), 166.8 (s), 165.6 (s), 157.1 (s), 152.1 (s), 146.4, 145.4, 139.2, 129.6, 128.5, 119.6, 118.7, 114.1, 101.9 (s), 99.1 (s), 79.1, 74.2, 73.7, 73.1, 71.6, 70.2, 68.5, 65.7, 64.8, 51.0 (quartet, 2 carbons), 44.9 (s), 44.3, 423.3, 42.0, 41.1 (s), 40.0, 36.5, 36.0, 35.1, 33.4, 31.4, 24.6, 21.9, 21.1, 19.8, 16.9 and 13.7.

Proton NMR (400 MHz, CDCl$_3$): δ 7.29–7.22 (m, 1H), 6.15 (d, J=5.6 Hz, 2H), 5.98 (s, 1H), 5.79 (d, J=3.4 Hz, 1H), 5.76 (d, J=3.6 Hz, 1H), 5.65 (s, 1H), 5.29 (m, 1H), 5.19 (m, 4H), 4.19 (m, 1–2H), 4.09 (m, 2H), 3.99 (m, 2H), 3.73 (m, 1H), 3.68 (s, 3H), 3.65 (s, 3H), 3.63 (m, 1H), 2.51 (t, J=12 Hz, 1H), 2.38 (d, J=10.5 Hz, 1H), 2.17–1.49 (complex, 11–12H), 2.05 (s, 3H), 1.44 (m, 3H), 1.22 (d, J=6.3 Hz, 3H), 1.13 (s, 3H), 0.98 (s, 6H), 0.91 (s, 3H) and 0.89 (d, J=7.3 Hz, 3H).

Analytical Data: Found: C, 61.55; H, 7.33 no nitrogen or sulfur present. C, 61.84; H, 7.22. Possible empirical formula of C$_{47}$H$_{68}$O$_{17}$; Calcd for C, 62.37 and H, 7.57.

Bryostatin 2

Appearance—Colorless, crystalline solid from methylene chloridemethanol.

Melting Point—201°–203° C., uncorrected.

| Thin Layer Chromatography Solvent System | Rf |
| --- | --- |
| CH$_2$Cl$_2$:MeOH (9:1) | 0.54 |

Ultraviolet Spectrum: λ max (MeOH)=230 nm (ε 36,250) and 261 nm (ε 35,600).

Optical Rotation: [α]$_{D25°\ C.}$ of a 5% solution in methanol is +50.0°.

Electron Impact Mass Spectrum (EIMS): m/e 826 (M-2 H$_2$O), exact mass 826.4138 amu (calcd. 826.4136 for C$_{45}$H$_{62}$O$_{14}$).

Infrared Spectrum (KBr): Peaks are seen at: 3465, 2975–2950, 1715 (strongest band), 1700, 1640–1650, 1435, 1360, 1250, 1230, 1165, 1100, 1080, 1050 and 1000 cm$^{-1}$.

C NMR: δ 172.74, 167.12, 166.89, 165.66, 156.95, 152.01, 146.49, 145.58, 139.18, 129.65, 128.45, 119.68, 118.64, 114.32, 101.90, 99.11, 79.16, 74.12, 73.83, 71.65, 70.12, 68.50, 66.06, 64.76, 51.11, 44.94, 44.22, 42.21, 42.21, 42.21, 40.07, 36.56, 35.94, 35.06, 31.36, 24.66, 21.90, 21.09, 19.76, 15.60, 13.68.

Proton NMR (400 MH$_3$, CDCl$_3$): δ, 7.2 (m, 1H), 6.16 (d, J=5.6 Hz), 6.01 (s, 1H), 5.81 (d, J=6.4 Hz, 1H), 5.77 (d, J=7.1 Hz, 1H), 5.68 (s, 1H), 5.31 (m, J=5 Hz, 1H), 5.19 (s, 2H), 4.28 (m, 1H), 4.16 (m, 2H), 3.99 (m, 3 or 4H), 3.80 (m, 1 or 2H), 3.70 (s, 3H), 3.66 (s, 3H), 3.63 (m, 1H), 2.46 (m, 2H), 2.21–1.57 (complex, 18–19H), 1.45 (m, 3H), 1.23 (d, J=6.3 Hz, 3 Hz), 1.15 (s, 3H), 1.04 (s, 3H), 1.00 (s, 3H), 0.92 (d, J=7.3 Hz, 3H), 0.91 (s, 3H).

Analytical Data: Found: C, 59.06; H, 7.16; O, 32.19. No nitrogen or sulfur present. Tentative formula: C$_{45}$H$_{66}$O$_{16}$.

Bryostatin 3

Appearance—White amorphous solid from methylene chloride-methanol.

Thin Layer Chromatography Solvent System—CH$_2$Cl$_2$:MeOH (93:7), R$_f$=0.56.

Ultraviolet Spectrum—λ max (MeOH)=229 (ε 31,700) and 264 (ε 30,600).

Optical Rotation—[α]$_{D25}$+61° (c, 0.26 in methanol).

FAB Mass Spectrum—m/e 911 (M+Na); M=C$_{46}$H$_{64}$O$_{17}$.

Infrared Spectrum (KBr)—3450, 2930–2970, 1785, 1740, 1718, 1640–1650, 1365, 1305, 1250, 1165, 1150, 1135, 1100, 1045–1075, 1000 cm$^{-1}$.

C NMR—172.48, 171.96, 171.18, 167.12, 166.89, 165.98, 157.11, 147.72, 146.65, 136.38, 132.77, 128.38, 117.37, 114.38, 114.12, 101.90, 101.71, 81.24, 73.05, 73.05, 71.46, 69.77, 69.12, 68.60, 68.30, 65.58, 51.18, 45.23, 44.19, 41.82, 41.82, 41.14, 39.48, 36.43, 35.13, 35.13, 33.24, 33.24, 33.24, 24.50, 21.87, 21.15, 21.15, 19.30, 16.99, 13.68;

Proton NMR (400 MHz, CDCl$_3$), δ 7.37—(m, 1H), 6.20 (m, 2H), 5.87 (d, 1H), 5.83 (s, 1H), 5.74 (s, 1H), 5.70 (d, 1H), 5.67 (s, 1H), 5.41 (m, 1H), 5.28 (s, 1H), 5.16 (m, 1H), 5.02 (m, 1H), 4.47 (m, 1H), 4.34 (m, 1H), 4.17 (m, 2H), 4.03–398 (m, 2H), 3.78 (m, 1H), 3.71 (m, 1H), 2.55 (m, 1H), 2.43 (m, 1H), 2.17 (m, 2–3H), 2.06 (s, 3H), 2.0 (m, 2H), 1.86 (m, 1H), 1.72 (m, 2H), 1.63 (m, 2H), 1.55 (m, 1–2H), 1.47 (m, 2H), 1.21 (d, J=6 Hz 3H), 1.12 (s, 3H), 1.00 (s, 6H), 0.92 (s, t, J=7 Hz 6H).

Determination of the Structure of Bryostatin 1

All crystallographic calculations were done on a PRIME 850 computer, operated by the Cornell Chemistry Computing Facility. Principal programs employed were REDUCE and UNIQUE, data reduction programs.

Stout parallelipiped crystals were obtained from slow mixing of a layered solution of bryostatin 1 in methylene chloride under methanol. When maintained in the mother liquor these crystals were found to belong to space group P2$_1$2$_1$2$_1$ with a=21.782(5), b=20.428(4) and c=23.664(6) Å Z=8. Upon drying the C-axis appeared to halve and the relatively poor diffraction pattern conformed to P2$_1$2$_1$2 [a similar type of pseudosymmetry has been observed for the hydrochloride of gramicidin S: Hodgkin, D. C.; Oughton, B. M., *Biochem. J.* 1957, 65, 725–756]. A total of 5464 reflections was collected at −100° C. using 1° ω-scans and graphite-monochromated Mo Kα: (0.71069 Å) radiation. Of these data, 3553 (65%) were judged observed [|F$_0$|>3σ(F$_0$)] and used in subsequent calculations. By means of the program system MULTAN78, approximately 2000 phase sets were generated for the largest 350 normalized structure factors, and the sets were ranked placing equal weight on ABSFOM, PSIZERO, RESID, and NQEST. E-syntheses using one of the most promising sets provided two chemically sensible and identical 24 atom fragments which were related by a translation of approximately c/2. Efforts to extend this model by tangent formula recycling [Karle, *J. Acta. Crystallogr.* Sect. B 1968, B24, 182–186] and/or attempts to refine this model in least squares were unsuccessful. Thus, we returned to tangent formula recycling using a scale factor which was the average of the Wilson pilot and the least squares scale factors. An E-synthesis from this approach was strikingly improved and showed 100 chemically sensible atoms in two essentially identical fragments. Further tangent formula recycling showed virtually all of the nonhydrogen atoms in both molecules of bryostatin 1.

Refinement of the final model by block-diagonal least squares alternating with Fourier syntheses using (2F$_{obs}$−F$_{calc}$) as coefficients [Main, P., *Acta Crystallogr.* Sect.

A 1979, A35, 779-785] led to the placement of 128 non-hydrogen atoms in the two independent molecules and determination of the structure of bryostatin 1 as illustrated in Chart I. The current x-ray model includes 59 anisotropic nonhydrogen atoms per molecule, and end atoms on the ester side chains which are isotropic (B's in the range 5 to 20 Å, average B approximately 2.5 Å), several solvent methanol molecules and 114 hydrogens at calculated positions. The standard crystallographic residual (R-factor) for this model has converged to 0.07 for the observed data.

As anticipated from the pseudosymmetry of the crystal, both independent molecules of bryostatin 1 have identical stereostructures and essentially identical conformations [For more detail see: Arnold, E., Ph.D. Dissertation, Cornell University, May, 1982]. The relative stereochemical designations of the eleven chiral centers in bryostatin 1 are: 3(R*), 5(R*), 7(S*), 9(S*), 11(S*), 15(R*), 19(S*), 20(S*), 23(S*), 25(R*), and 26(R*). The crystal conformation of bryostatin 1 defines a roughly scoop-shaped molecule with length 13 Å, width 8 Å, and height approximately 6 Å. Examination of molecular models suggests that there are other plausible conformations.

The enantiomer of bryostatin 1 shown in Chart I was selected as follows: The method of Engel (Engel, D. W., *Acta Crystallogr.* Sect. B, 1972, B28: 1498-1509) was used to measure anomalous scattering effects due to oxygen and carbon ($\Delta f'=0.032$ and $\Delta f'=0.009$ electrons, respectively, for Cu K$\alpha$ data collection). Seven groups of Bijvoet pairs which were expected to have the largest Bijvoet ratios were measured (3x) very slowly using Cu K$\alpha$ radiation. Neighboring pairs, which in each case were centrosymmetric reflections, were measured in a similar manner to provide an empirical correction for absorption and other anisotropic effects. The absorption-corrected Bijvoet ratios which were obtained for each of the seven groups indicated the enantiomer.

Bryostatin 1 may be considered as a 26-membered macrolide ring. Embedded in the 26-membered ring is a 20-membered cycle defined by taking the shorter path through the pyran oxygens rather than along the carbon chain. The longest chain of carbon atoms is 27 and has been used in the proposed numbering system. The oxygen substitution pattern, augmented by the gem-dimethyl substituents at carbons 8 and 18, suggests a polyketide biosynthesis for bryostatin 1. All three pyran rings are approximately in the chain conformation and each has a 4-position substituent which projects outward. All of the macrocycle substituents are equatorial with reference to the pyran rings. An intramolecular hydrogen bond appears between 019H and 03 (2.71, 2.71 Å), and two possible hydrogen bonds are found between 03H and 05 (2.84, 2.87 Å), and between 03H and 011 (3.00, 3.02 Å).

In the crystalline conformation oxygens 01, 03, 05, 011, 019A, and 019B are all on the interior of the large, oxygen-rich cavity in bryostatin 1. The size and shape of this cavity, and the arrangement of oxygen atoms suggests that the molecule may have cation-binding capabilities, similar to the polyether antibiotics. The axial (E,E)octa-2,4-dienoic acid substituent at C20 would be expected to enhance lipid solubility. An intriguing possibility is that this substituent could swing over the internal cavity by rotation about the C20-020 bond and 'seal' one side. The stereochemistry of the two acetylidene units in bryostatin 1 at C13 and C21 is such that the carbonyl oxygen points in the direction of increasing carbon number along the macrocycle. While these units are disubstituted at the $\beta$-carbon, it is conceivable that they could function as Michael acceptors for bipolymer amine and/or thiol groups.

Determination of the Structure of Bryostatin 2

As bryostatin 2 could not be obtained in a crystalline form suitable for x-ray crystal structure determination, unequivocal assignment of the structure shown in Chart II required analysis of the high resolution proton magnetic resonance spectra of bryostatins 1 and 2 supported by the results of $^{13}$C NMR (CDCl$_3$), mass, and other spectral investigations. The 400 MHz $^1$H NMR spectra of bryostatins 1 and 2 in CDCl$_3$ were tentatively assigned by extensive double resonance experiments (Chart V). The proton spectrum of bryostatin 2 was nearly identical to that of bryostatin 1 except for the absence of the acetate methyl resonance at 2.05 ppm and the upfield shift of the C7 proton from 5.15 to 3.15 ppm. These observations suggested that bryostatin 2 was the desacetyl analog of bryostatin 1. The conclusion was strengthened by noting that the $^{13}$C NMR spectrum of bryostatin 2 did not differ significantly from that of bryostatin 1 except for the loss of the acetyl carbonyl (171.15 ppm) and methyl (33.44) resonances, the upfield shift of an oxygen-bearing carbon (presumably C7) from 73.11 to 70.12, the downfield shift of a quaternary carbon from 41.11 to 42.21 (presumably C8), and a small shift in the position of one of the gem-dimethyl group resonances (presumably C28 or C29).

Confirmation of the bryostatin 2 structure was obtained by a series of selective micro-scale acetylation-deacetylation experiments. The identical (by TLC) acetate (colorless needles from CH$_2$Cl$_2$-MeOH, mp 249°-250° C.) was obtained by partial acetylation (acetic anhydride-pyridine, 2 hr, room temperature) of bryostatin 1 and 2. Careful deacetylation of the acetate with hydrochloric acid (1%) in methanol (24 hr, room temperature) or with potassium carbonate (1%) in methanol (24 hr, room temperature) afforded a mixture of bryostatins 1 and 2. Because the structure of bryostatin 1 was assigned by an x-ray crystal structure determination, the combination of evidence from high resolution NMR analyses and conversion to the acetate established the structure of bryostatin 2.

Determination of the Structure of Bryostatin 3

Bryostatin 3 was isolated as an amorphous solid. Assignment of structure was based on analysis of the 400 MHz $^1$H NMR and $^{13}$C NMR spectra as well as on the infrared and mass spectral measurements. These are as follows:

| Position | $^{13}$C NMR | $^1$H NMR | Multiplicity (J = Hz) |
| --- | --- | --- | --- |
| 1 | 172.48 | — | |
| 2 | 44.19 | 2.43, 2.55 | m |
| 3 | 69.77 | 4.03 | m |
| 4 | 33.24 | 1.55, 1.9 | m |
| 5 | 71.46 | 4.17 | m |
| 6 | 33.24 | 1.4, 1.72 | m |
| 7 | 73.05 | 5.16 | m |
| 8 | 41.14 | — | |
| 9 | 101.90 | — | |
| 10 | 35.13 | 2.17 | m |
| 11 | 68.60 | 3.98 | m |
| 12 | 36.43 | 2.17 | m |
| 13 | 157.11 | — | |
| 14 | 39.48 | 2.06 | m |

-continued

| Position | 13C NMR | 1H NMR | Multiplicity (J = Hz) |
|---|---|---|---|
| 15 | 69.12 | 4.17 | m |
| 16 | 136.38 | 5.41 | dd (8, 14) |
| 17 | 132.77 | 5.70 | d (14) |
| 18 | 45.23 | — | |
| 19 | 101.71 | — | |
| 20 | 81.24 | 5.82 | s |
| 21 | 41.82 | 1.85 | m |
| 22 | 114.12 | 5.74 | s |
| 23 | 166.89 | — | |
| 24 | 41.82 | 1.86, 2.35 | m |
| 25 | 73.05 | 5.02 | m |
| 26 | 65.58 | 3.78 | m |
| 27 | 21.87 | 1.21 | d (6) |
| 28 | 21.15* | 1.12* | s |
| 29 | 16.99* | 1.00* | s |
| 30 | 114.38 | 5.67 | s |
| 31 | 167.12 | — | |
| 32 | 21.15* | 1.00* | s |
| 33 | 19.30* | 0.92* | s |
| 34 | 68.30 | 3.71 | d (9) |
| 35 | 171.96 | — | |
| 36 | 171.18 | — | |
| 37 | 33.24 | 2.05 | s |
| 38 | 51.18 | 3.69 | s |
| 39 | 165.98 | — | |
| 40 | 117.37 | 5.87 | d (15) |
| 41 | 147.72 | 7.37 | m |
| 42 | 128.38 | 6.20 | m |
| 43 | 146.65 | 6.20 | m |
| 44 | 35.13 | 2.17 | m |
| 45 | 24.50 | 1.47 | m |
| 46 | 13.68 | 0.92 | t (7) |
| 34-OH | | 4.47 | d (9) |
| 3-OH | | 4.34 | d (13) |

*Assignments for these four groups may be interchanged.

Analysis of the FAB mass spectra of bryostatin 1 and 3 indicated a net loss of 16 mass units for bryostatin 3. Furthermore the FAB fragmentation pattern involving loss of the acetate and octa-2,4-dienoate side chains of bryostatin 1 was repeated in the spectrum of bryostatin 3. The similarity of optical rotations and ultraviolet spectra exhibited by bryostatins 1–3 also suggested that the new macrocyclic lactone resembled its companions. The 13C NMR spectra led to the same overall conclusion and indicated that bryostatins 1–3 contained the same bryopyran ring system. However, some signal shifts (1–3 ppm) and other differences were noted. Signals previously assigned to carbons C-21 and C-47 of bryostatins 1 and 2 were missing and that due to C-35 appeared to undergo a downfield shift from 166.8 to 171.9 ppm. The 13C NMR spectrum of lactone 2 also contained new signals at 41.82, 68.30, 114.12 and 166.73 ppm now believed to correspond to C-21, C-34, C-22 and C-23 respectively.

Careful interpretation of the infrared and high resolution (400 MHz) 1H NMR spectra (decoupling experiments) allowed a definite structural assignment for bryostatin 3. The new infrared absorption band at 1785 cm$^{-1}$ exhibited by bryopyran 2 indicated a possible 5- or 6-membered lactone carbonyl group with an alpha electronegative substituent. Comparison of the 1H NMR spectra showed loss of the C-22 and C-23 protons of bryostatins 1 and 2. And protons assigned to C-15-17, C-20, C-24 and C-40-43 were shifted downfield from those of bryostatin 1 by 0.01–0.05 ppm. An upfield shift of about the same magnitude was viewed for the C-17 and C-25 protons. The C-24 proton was strongly displaced downfield from 2.0 to 2.35 δ. Very importantly, new signals appeared in the spectrum of bryostatin 3 at 5.82 δ (C-22) and at 3.71 δ (C-34). The latter was coupled to protons at 1.85 δ (C-21) and at 4.47 δ (—OH at C-34). From these NMR interpretations it was clear that the fundamental bryopyran ring system was still represented in bryostatin 3. Indeed, except for a profound change in the bryopyran C-ring and the shifts noted above, the remainder of bryostatin 3 was found essentially identical with bryostatin 1. A shift (C-21,34→C-22,23) in the exocyclic ring C olefin of bryostatin 1 to a dihydropyran system, hydroxylation at C-34, and lactonisation of the C-35 carbonyl of the lactate side-chain with the C-19 hemiketal hydroxyl group provided a most satisfactory explanation of the bryostatin 3 to bryostatin 1 relationship. The preceding observations combined with the unequivocal x-ray crystal structure determination of bryostatin 1 allowed the structure to be assigned to bryostatin 3.

Since bryostatin 3 retains the very potent antineoplastic activity of bryostatin 1 loss of one pyran acetylidene group does not appear critical.

| | Antineoplastic Activity[d] Mouse Tumor System | | |
|---|---|---|---|
| | P388 leukemia[a] (PS System) | | |
| Compound | toxic dose in μg/kg/day injection | optimal dose in μg/kg/day injection[b] | life span at optimal dose in percent of controls[c] |
| Bryostatin 1 | 310 | 70 | 196 |
| Bryostatin 2 | 60 | 30 | 160 |
| Bryostatin 3 | 60 | 30 | 163 |

[a]tumors were inoculated intraperitoneally (i.p.)
[b]compounds were administered i.p. every day for 9 days starting on the first day after tumor inoculation.
[c]Calculated from median survival times.
[d]A description of the antitumor tests appears in the reference by R. I. Geran, N. H. Greenberg, M. M. MacDonald, A. M. Schumacher and B. J. Abbott, Cancer Chemother. Rep. Part 3, Vol. 3(2): 1–103 (1972).

The tests are predictive of anticancer activity in other mammals including man. It is expected that the bryostatins 1, 2, and 3 either alone or in combination with other known anticancer compounds will have therapeutic value in treating neoplastic diseases such as acute myelocytic leukemia, acute lymphocytic leukemia, malignant melanoma, adenocarcinoma of lung, neuroblastoma, small cell carcinoma of lung, breast carcinoma, colon carcinoma, ovarian carcinoma, bladder carcinoma, and the like.

The dosage administered will be dependent upon the identity of the neoplastic disease, the type of host involved, its age, health, weight, kind of concurrent treatment, if any, frequency of treatment and therapeutic ratio.

Illustratively, dosage levels of the administered active ingredients can be: intravenous, 0.1 to about 200 mg/kg; intraperitoneal, 1 to about 500 mg/kg; subcutaneous, 1 to about 500 mg/kg; intramuscular, 1 to about 500 mg/kg; orally, 5 to about 1000 mg/kg; intranasal instillation, 5 to about 1000 mg/kg; and aerosol, 5 to about 1000 mg/kg of animal (body) weight.

Expressed in terms of concentration, an active ingredient can be present in the compositioms of the present invention for localized use about the cutis, intranasally, pharyngolaryngeally, bronchially, broncholially, intravaginally, rectally, or ocularly in a concentration of from about 0.01 to about 50% w/w of the composition; preferably about 1 to about 20% w/w of the composition; and for parenteral use in a concentration of from about 0.05 to about 50% w/v of the composition and preferably from about 5 to about 20% w/v.

The compositions of the present invention are preferably presented for administration to humans and animals in unit dosage forms, such as tablets, capsules, pills, powders, granules, suppositories, sterile parenteral solutions or suspensions, sterile non-parenteral solutions or suspensions, and oral solutions or suspensions and the like, containing suitable quantities of an active ingredient.

For oral administration either solid or fluid unit dosage forms can be prepared.

Powders are prepared quite simply by comminuting the active ingredient to a suitably fine size and mixing with a similarly comminuted diluent. The diluent can be an edible carbohydrate material such as lactose or starch. Advantageously, a sweetening agent or sugar is present as well as a flavoring oil.

Capsules are produced by preparing a powder mixture as hereinbefore described and filling into formed gelatin sheaths. Advantageously, as in adjuvant to the filling operation, a lubricant such as a talc, magnesium stearate, calcium stearate and the like is added to the powder mixture before the filling operation.

Soft gelatin capsules are prepared by machine encapsulation of a slurry of active ingredients with an acceptable vegetable oil, light liquid petrolatum or other inert oil or triglyceride.

Tablets are made by preparing a powder mixture, granulating or slugging, adding a lubricant and pressing into tablets. The powder mixture is prepared by mixing an active ingredient, suitably comminuted, with a diluent or base such as starch, lactose, kaolin, dicalcium phosphate and the like. The powder mixture can be granulated by wetting with a binder such as corn syrup, gelatin solution, methylcellulose solution or acacia mucilage and forcing through a screen. As an alternative to granulating, the powder mixture can be slugged, i.e., run through the tablet machine and the resulting imperfectly formed tablets broken into pieces (slugs). The slugs can be lubricated to prevent sticking to the tablet-forming dies by means of the addition of stearic acid, a stearic salt, talc or mineral oil. The lubricated mixture is then compressed into tablets.

Advantageously the tablet can be provided with a protective coating consisting of a sealing coat or enteric coat of shellac, a coating of sugar and methylcellulose and polish coating of carnauba wax.

Fluid unit dosage forms for oral administration such as syrups, elixirs and suspensions can be prepared wherein each teaspoonful of composition contains a predetermined amount of active ingredient for administration. The water-soluble forms can be dissoled in an aqueous vehicle together with sugar, flavoring agents and preservatives to form a syrup. An elixir is prepared by using a hydroalcoholic vehicle with suitable sweeteners together with a flavoring agent. Suspensions can be prepared of the insoluble forms with a suitable vehicle with the aid of a suspending agent such as acacia, tragacanth, methylcellulose and the like.

For parenteral administration, fluid unit dosage forms are prepared utilizing an active ingredient and a sterile vehicle, water being preferred. The active ingredient, depending on the form and concentration used, can be either suspended or dissolved in the vehicle. In preparing solutions the water-soluble active ingredient can be dissolved in water for injection and filter sterilized before filling into a suitable vial or ampule and sealing. Advantageously, adjuvants such as a local anesthetic, preservative and buffering agents can be dissolved in the vehicle. Parenteral suspensions are prepared in substantially the same manner except that an active ingredient is suspended in the vehicle instead of being dissolved and sterilization cannot be accomplished by filtration. The active ingredient can be sterilized by exposure to ethylene oxide before suspending in the sterile vehicle. Advantageously, a surfactant or wetting agent is included in the composition to facilitate uniform distribution of the active ingredient.

In addition to oral and parenteral administration, the rectal and vaginal routes can be utilized. An active ingredient can be administered by means of a suppository. A vehicle which has a melting point at about body temperature or one that is readily soluble can be utilized. For example, cocoa butter and various polyethylene glycols (Carbowaxes) can serve as the vehicle.

For intranasal instillation, fluid unit dosage forms are prepared utilizing an active ingredient and a suitable pharmaceutical vehicle, water being preferred, or by dry powder for insufflation.

For use as aerosols the active ingredients can be packaged in a pressurized aerosol container together with a gaseous or liquefied propellant, for example, dichlorodifluoromethane, carbon dioxide, nitrogen, propane, and the like, with the usual adjuvants such as cosolvents and wetting agents, as may be necessary or desirable.

The term "unit dosage form" as used in the specification and claims refers to physically discrete units suitable as unitary dosages for human and animal subjects, each unit containing a predetermined quantity of active material calculated to produce the desired therapeutic effect in association with the required pharmaceutical diluent, carrier or vehicle. The specifications for the novel unit dosage forms of this invention are dictated by and are directly dependent on (a) the unique characteristics of the active material and the particularly therapeutic effect to be achieved, and (b) the limitation inherent in the art of compounding such an active material for therapeutic use in humans, as disclosed in this specification, these being features of the present invention. Examples of suitable unit dosage forms in accord with this invention are tablets, capsules, troches, suppositories, powder packets, wafers, cachets, teaspoonfuls, tablespoonfuls, dropperfuls, ampuls, vials, segregated multiples of any of the foregoing, and other forms as herein described.

The active ingredients to be employed as anti-viral or anti-neoplastic agents can be easily prepared in unit dosage form with the employment of pharmaceutical materials which themselves are available in the art and can be prepared by established procedures. The following preparations are illustrative of the preparation of the unit dosage forms of the present invention, but are not intended to be limiting.

COMPOSITION EXAMPLE 1

Hard-Gelatin Capsules

One thousand two-piece hard gelatin capsules for oral use, each capsule containing 200 mg of a bryostatin are prepared from the following types and amounts of ingredients:

a bryostatin micronized: 200 gm
Corn Starch: 20 gm
Talc: 20 gm
Magnesium stearate: 2 gm The bryostatin finely divided by means of an air micronizer, is added to the other finely powdered ingredients, mixed thoroughly and then encapsulated in the usual manner.

The foregoing capsules are useful for treating a neoplastic disease by the oral administration of one or two capsules one to four times a day.

Using the procedure above, capsules are similarly prepared containing a bryostatin in 50, 250 and 500 mg amounts by substituting 50 gm, 250 gm and 500 gm of a bryostatin for the 200 gm used above.

COMPOSITION EXAMPLE 2

Soft Gelatin Capsules

One-piece soft gelatin capsules for oral use, each containing 200 mg of a bryostatin (finely divided by means of an air micronizer), are prepared by first suspending the compound in 0.5 ml of corn oil to render the material capsulatable and then capsulating in the above manner.

The foregoing capsules are useful for treating a neoplastic disease by the oral administration of one or two capsules one to four times a day.

COMPOSITION EXAMPLE 3

Tablets

One thousand tablets, each containing 200 mg of a bryostatin are prepared from the following types and amounts of ingredients:

A bryostatin, micronized: 200 gm
Lactose: 300 gm
Corn starch: 50 gm
Magnesium stearate: 4 gm
Light liquid petrolatum: 5 gm The bryostatin finely divided by means of an air micronizer, is added to the other ingredients and then thoroughly mixed and slugged. The slugs are broken down by forcing through a Number Sixteen screen. The resulting granules are then compressed into tablets, each tablet containing 200 mg of the bryostatin.

The foregoing tablets are useful for treating a neoplastic disease by the oral administration of one or two tablets one to four times a day.

Using the procedure above, tablets are similarly prepared containing a bryostatin in 250 mg and 100 mg amounts by substituting 250 gm and 100 gm of a bryostatin for the 200 gm used above.

COMPOSITION EXAMPLE 4

Oral Suspension

One thousand ml of an aqueous suspension for oral use, containing in each teaspoonful (5 ml) dose, 50 mg of a bryostatin, is prepared from the following types and amounts of ingredients:

A bryostatin, micronized: 10 gm
Citric acid: 2 gm
Benzoic acid: 1 gm
Sucrose: 790 gm
Tragacanth: 5 gm
Lemon Oil: 2 gm
Deionized water, q.s. 1000 ml.

The citric acid, benzoic acid, sucrose, tragacanth and lemon oil are dispersed in sufficient water to make 850 ml of suspension. The bryostatin, finely divided by means of an air micronizer, is stirred into the syrup until uniformly distributed. Sufficient water is added to make 1000 ml.

The composition so prepared is useful for treating a neoplastic disease at a dose of 1 tablespoonful (15 ml) three times a day.

COMPOSITION EXAMPLE 5

A sterile aqueous suspension for parenteral injection, containing in 1 ml 300 mg of a bryostatin for treating a neoplastic disease, is prepared from the following types and amounts of ingredients:

A bryostatin, micronized: 30 gm
Polysorbate 80: 5 gm
Methylparaben: 2.5 gm
Propylparaben: 0.17 gm
Water for injection, q.s. 1000 ml.

All the ingredients, except the bryostatin, are dissolved in the water and the solution sterilized by filtration. To the sterile solution is added the sterilized bryostatin, finely divided by means of an air micronizer, and the final suspension is filled into sterile vials and the vials sealed.

The composition so prepared is useful for treating a neoplastic disease at a dose of 1 milliliter (1M) three times a day.

COMPOSITION EXAMPLE 6

Suppository, Rectal and Vaginal

One thousand suppositories, each weighing 2.5 gm and containing 200 mg of a bryostatin are prepared from the following types and amounts of ingredients:

A bryostatin, micronized: 15 gm
Propylene glycol: 150 gm
Polyethylene glycol: #4000, q.s. 2,500 gm The bryostatin is finely divided by means of an air micronizer and added to the propylene glycol and the mixture passed through a colloid mill until uniformly dispersed. The polyethylene glycol is melted and the propylene glycol dispersion added slowly with stirring. The suspension is poured into unchilled molds at 40° C. The composition is allowed to cool and solidify and then removed from the mold and each suppository foil wrapped.

The foregoing suppositories are inserted rectally or vaginally for treating a neoplastic disease.

COMPOSITION EXAMPLE 7

Intranasal Suspension

One thousand ml of a sterile aqueous suspension for intranasal instillation, containing in each ml 200 mg of a bryostatin, is prepared from the following types and amounts of ingredients:

A bryostatin, micronized: 15 gm
Polysorbate 80: 5 gm
Methylparaben: 2.5 gm
Propylparaben: 0.17 gm
Deionized water, q.s. 1000 ml.

All the ingredients, except the bryostatin, are dissolved in the water and the solution sterilized by filtration. To the sterile solution is added the sterilized bryostatin, finely divided by means of an air micronizer, and the final suspension is aseptically filled into sterile containers.

The composition so prepared is useful for treating a neoplastic disease, by intranasal instillation of 0.2 to 0.5 ml given one to four times per day.

An active ingredient can also be present, as shown in Examples 12-14 in the undiluted pure form for use locally about the cutis, intranasally, pharyngolaryngeally, bronchially, broncholially or orally.

COMPOSITION EXAMPLE 8

Powder

Five grams of a bryostatin in bulk form is finely divided by means of an air micronizer. The micronized powder is placed in a shaker-type container.

The foregoing composition is useful for treating a neoplastic disease, at localized sites by applying the powder one to four times per day.

COMPOSITION EXAMPLE 9

Oral Powder

One hundred grams of a bryostatin in bulk form is finely divided by means of an air micronizer. The micronized powder is divided into individual doses of 200 mg and packaged.

The foregoing powders are useful for treating a neoplastic disease, by the oral administration of one or two powders suspended in a glass of water, one to four times per day.

COMPOSITION EXAMPLE 10

Insufflation

One hundred grams of a bryostatin in bulk form is finely divided by means of an air micronizer.

The foregoing composition is useful for treating a neoplastic disease, by the inhalation of 300 mg one to four times per day.

COMPOSITION EXAMPLE 11

Hard Gelatin Capsules

One hundred two-piece hard gelatin capsules for oral use, each capsule containing 200 mg of a bryostatin.

The bryostatin is finely divided by means of an air micronizer and encapsulated in the usual manner.

The foregoing capsules are useful for treating a neoplastic disease, by the oral administration of one or two capsules one to four times a day.

Using the procedure above, capsules are similarly prepared containing bryostatin in 50, 250 and 500 mg amounts by substituting 50 gm, 250 gm and 500 gm of a bryostatin for the 200 gm used above.

CHART I

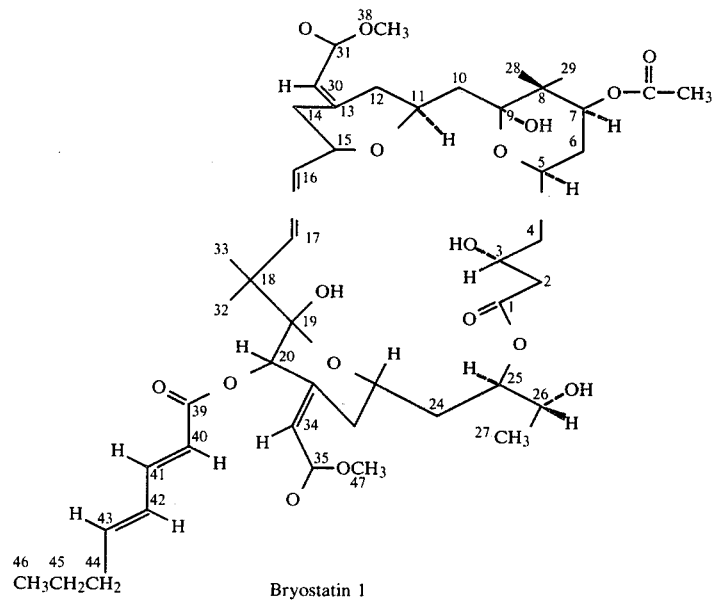

Bryostatin 1

CHART II

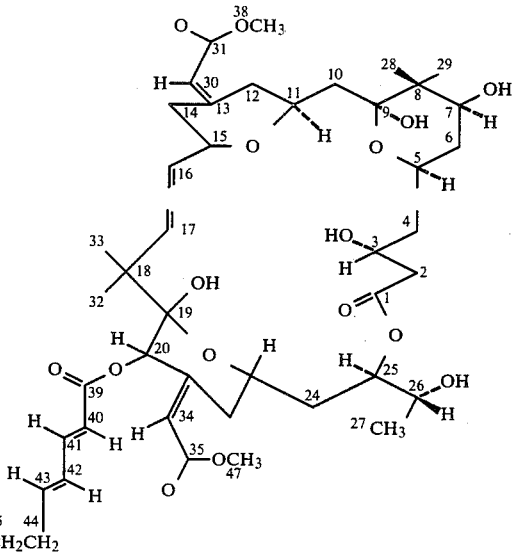

Bryostatin 2

CHART III
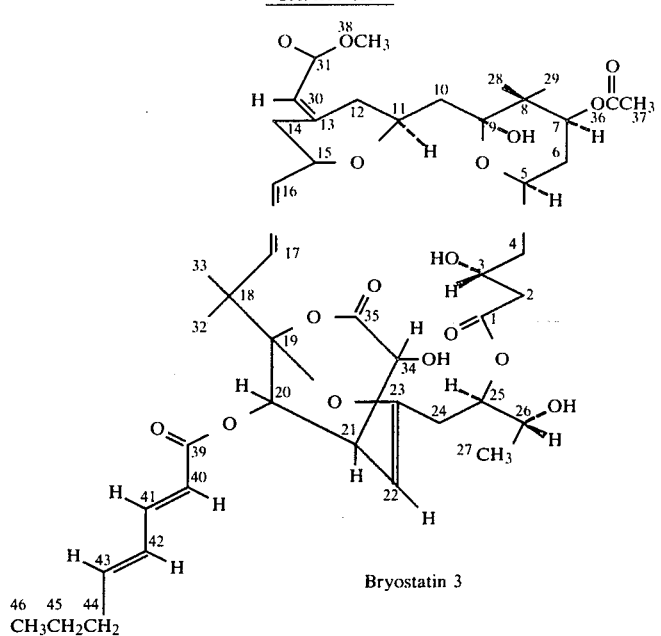
Bryostatin 3
CHART IV
Extraction and Solvent Partitioning of Marine Animal Constituents
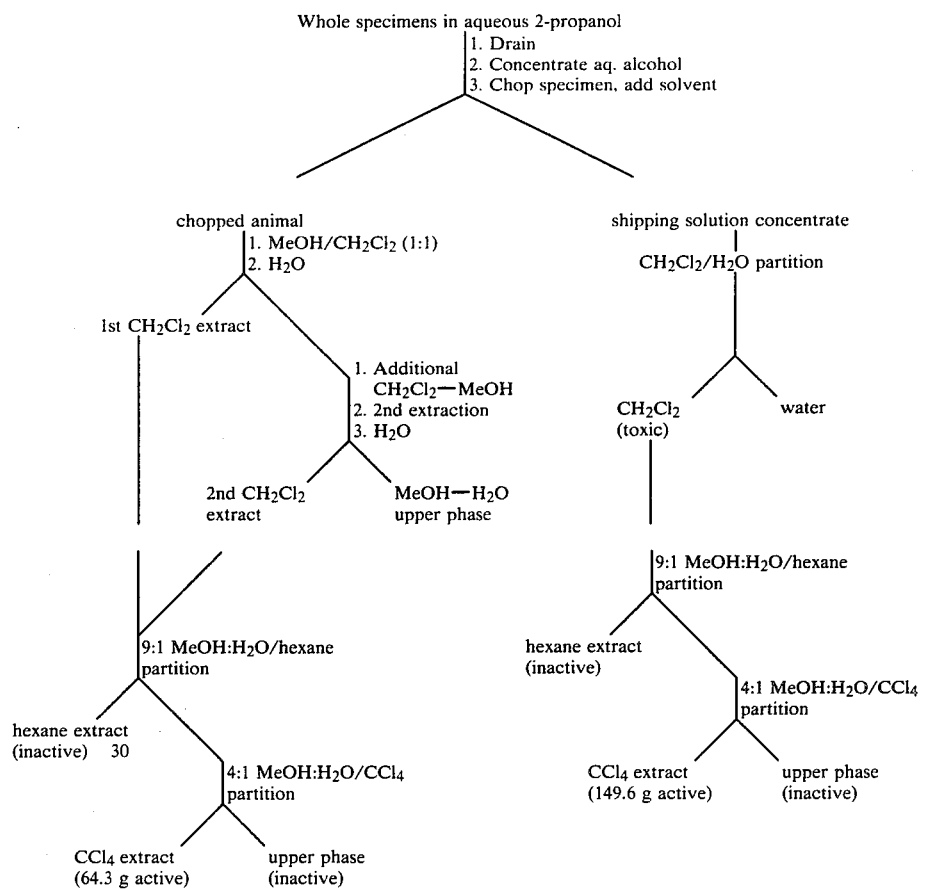

CHART V

| | 1H NMR Data for Bryostatins 1 and 2 | | | |
|---|---|---|---|---|
| | δ (ppm) | | Multiplicity (J Hz) | |
| Position | 1 | 2 | 1 | 2 |
| 2 | 2.45 | 2.45 | m | m |
| 3 | 4.19 | 4.13 | m | m |
| 4 | 1.55, 1.95 | 1.55, 1.95 | m | m, m |
| 5 | 4.1 | 4.13 | m | m |
| 6 | 1.4, 1.5 | 1.39, 1.65 | m, m | m, m |
| 7 | 5.15 | 3.95 | m | m |
| 10 | 2.1–2.2 | 2.1–2.2 | m | m |
| 11 | ~3.95 | 3.79 | m | m |
| 12 | 2.1–2.2 | 2.1–2.2 | m | m |
| 14 | 1.9, ~2.0 | 1.9, 2.0 | m | m |
| 15 | 4.08 | 4.02 | m | m |
| 16 | 5.300 | 5.287 | dd (8.3, 15.9) | dd (8.3, 15.8) |
| 17 | 5.758 | 5.753 | d (15.9) | d (15.8) |
| 20 | 5.162 | 5.162 | s | s |
| 22 | ~1.90 | ~1.90 | m | m |
| 23 | ~3.65 | ~3.65 | m | m |
| 24 | 1.95 | 1.95 | m | m |
| 25 | 5.19 | 5.12 | m | m |
| 26 | 3.73 | 3.78 | m | m |
| 27 | 1.226 | 1.207 | d (6.3) | d (6.1) |
| 28* | 1.132 | 1.123 | s | s |
| 29* | 0.982 | 1.009 | s | s |
| 30 | 5.657 | 5.654 | s | s |
| 32* | 0.982 | 0.978 | s | s |
| 33* | 0.919 | 0.877 | s | s |
| 34 | 5.983 | 5.982 | s | s |
| 37 | 2.051 | — | s | — |
| 40 | 5.796 | 5.776 | d (15.3) | d (15.3) |
| 41 | 7.261 | 7.242 | m | m |
| 42 | 6.157 | 6.142 | m | m |
| 43 | 6.157 | 6.142 | m | m |
| 44 | ~2.15 | ~2.15 | m | m |
| 45 | 1.42 | 1.42 | m | m |
| 46 | 0.904 | 0.894 | t (7.3) | t (7.3) |

*Assignments for these four groups may be interchanged.

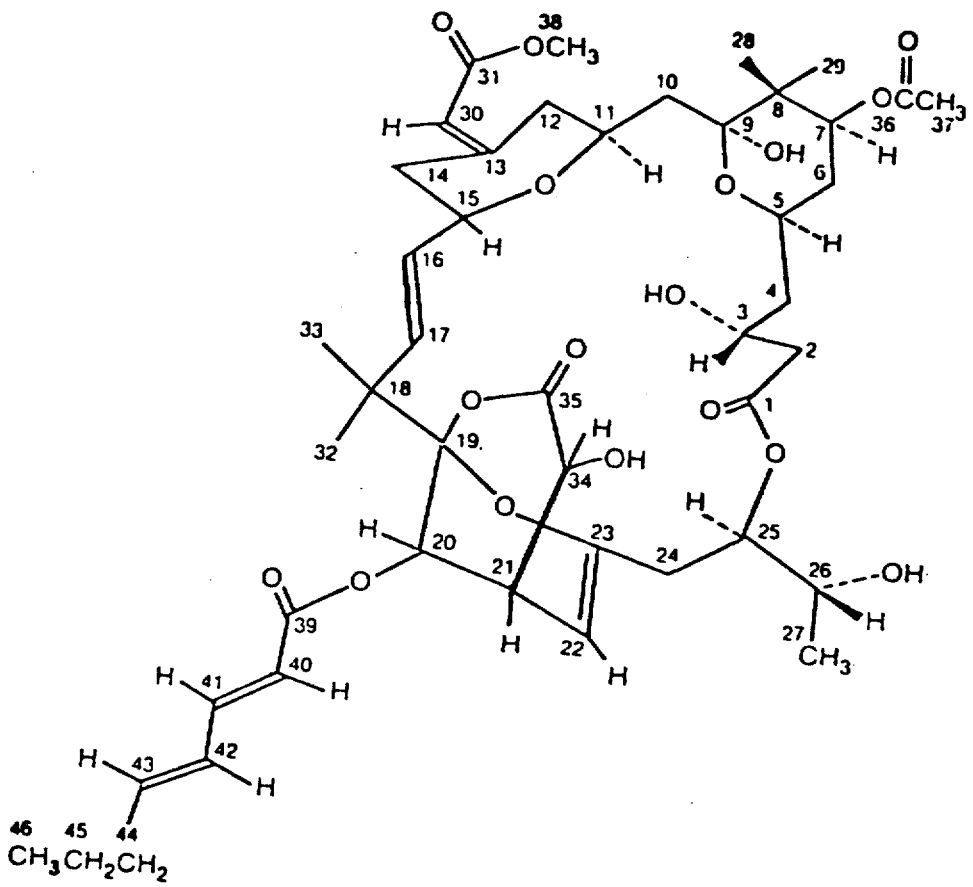

We claim:

1. A compound designated bryostatin 1 which has the following characteristics:
Melting Point: 230°–235°;
Optical Rotation: $[\alpha]_{D25°} +34.1°$ (C, 0.044, CH$_3$OH);
Ultra Violet Absorption Spectrum: (CH$_3$OH) λ max 233 (ε 25,700) and 263 nm (ε 28,700);
Infrared Absorption Spectrum (KBr): 3470, 3400, 2970, 2950, 1735, 1716, 1700, 1640, 1600, 1433, 1385, 1245, 1160, 1100, 1080, and 1000 cm$^{-1}$;
and which can be shown by the following structural formula:

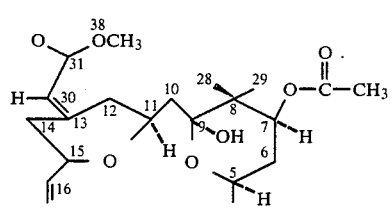
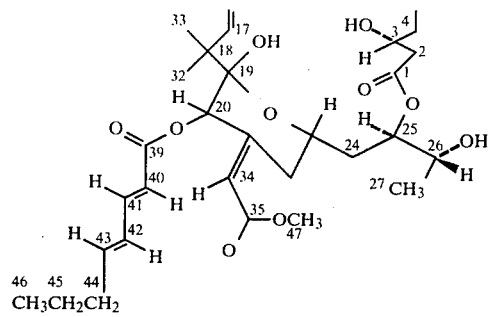

2. A compound designated bryostatin 2 which has the following characteristics:
Melting Point: 201°–203°;
Optical Rotation: $[\alpha]_{D25°} +50°$ (C=0.050, CH$_3$OH);
Ultra Violet Absorption Spectrum: (CH$_3$OH) λ max 230 (ε 36,250) and 261 (ε 35,600)nm;
Infrared Absorption Spectrum (KBr): 3465, 2975–2950, 1715, 1700, 1640–1650, 1435, 1360, 1250, 1230, 1165, 1100, 1080, 1050 and 1000 cm$^{-1}$;
and which can be shown by the following structural formula:

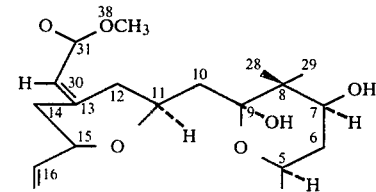
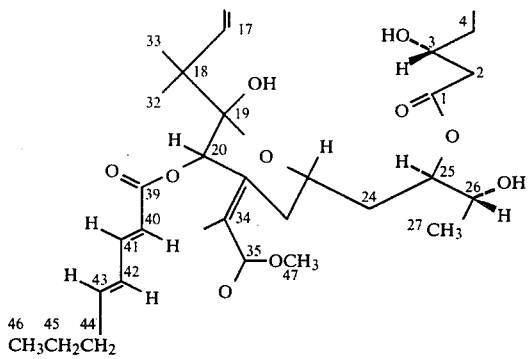

3. A compound designated bryostatin 3 which has the following characteristics:
Appearance—White amorphous solid from methylene chloride-methanol;
Thin Layer Chromatography Solvent System—CH$_2$Cl$_2$:MeOH (93:7), $R_f$=0.56;
Ultraviolet Spectrum—λ max (MeOH)=229 (ε 31,700) and 264 (ε 30,600);
Optical Rotation—$[\alpha]_{D25°} +61°$ (c, 0.26 in methanol);
FAB Mass Spectrum—m/e 911 (M+Na); M=C$_{46}$H$_{64}$O$_{17}$;
Infrared Spectrum (KBr)—3450, 2930–2970, 1785, 1740, 1718, 1640–1650, 1365, 1305, 1250, 1165, 1150, 1135, 1100, 1045–1075, 1000 cm$^{-1}$; $^{13}$C NMR—172.48, 171.96, 171.18, 167.12, 166.89, 165.98, 157.11, 147.72, 146.65, 136.38, 132.77, 128.38, 117.37, 114.38, 114.12, 101.90, 101.71, 81.24, 73.05, 73.05, 71.46, 69.77, 69.12, 68.60, 68.30, 65.58, 51.18, 45.23, 44.19, 41.82, 41.82, 41.14, 39.48, 36.43, 35.13, 35.13, 33.24, 33.24, 33.24, 24.50, 21.87, 21.15, 21.15, 19.30, 16.99, 13.68;
Proton NMR (400 MHz, CDCl₃), δ 7.37—(m, 1H), 6.20 (m, 2H), 5.87 (d, 1H), 5.83 (s, 1H), 5.74 (s, 1H), 5.70 (d, 1H), 5.67 (s, 1H), 5.41 (m, 1H), 5.28 (s, 1H), 5.16 (m, 1H), 5.02 (m, 1H), 4.47 (m, 1H), 4.34 (m, 1H), 4.17 (m, 2H), 4.03–398 (m, 2H), 3.78 (m, 1H), 3.71 (m, 1H), 2.55 (m, 1H), 2.43 (m, 1H), 2.17 (m, 2–3H), 2.06 (s, 3H), 2.0 (m, 2H), 1.86 (m, 1H), 1.72 (m, 2H), 1.63 (m, 2H), 1.55 (m, 1–2H), 1.47 (m, 2H), 1.21 (d, J=6 Hz 3H), 1.12 (s, 3H), 1.00 (s, 6H), 0.92 (s, t, J=7 Hz 6H);
and which can be shown by the following structural formula:
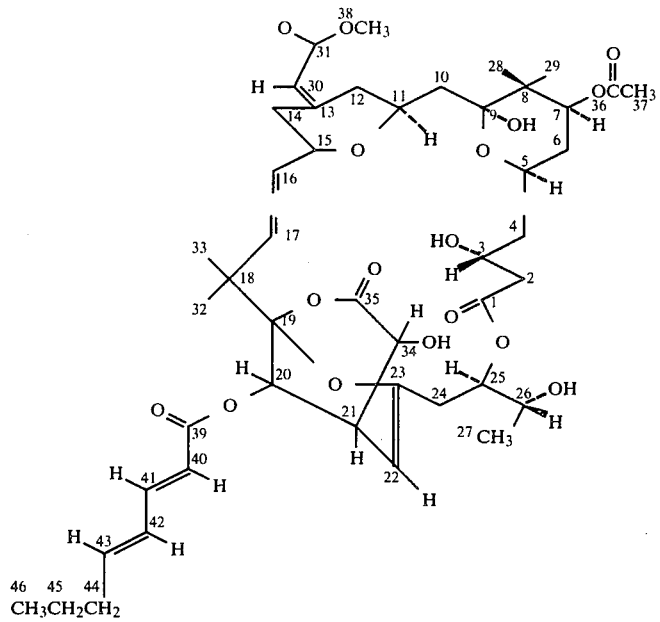
* * * * *

UNITED STATES PATENT OFFICE
CERTIFICATE OF CORRECTION

Patent No. 4,560,774    Dated 24 December 1985

Inventor(s) G.R. Pettit, et al.

It is certified that error appears in the above-identified patent and that said Letters Patent are hereby corrected as shown below:

Column 7, line 10, "423.3," should read -- 42.3, --.

Column 7, line 53, "(d, J=5.6 Hz)," should read -- (d, J=5.6 Hz, 2H), --.

Column 8, line 37, "ÅZ=8." should read -- Å and Z=8. --.

Column 14, line 36, "particularly" should read -- particular --.

Column 18, Chart I should appear as follows:

Signed and Sealed this

*Fifteenth* Day of *July 1986*

[SEAL]

Attest:

DONALD J. QUIGG

*Attesting Officer*    *Commissioner of Patents and Trademarks*

UNITED STATES PATENT OFFICE
CERTIFICATE OF CORRECTION

Patent No. 4,560,774                    Dated 24 December 1985

Inventor(s) G.R. Pettit, et al.

It is certified that error appears in the above-identified patent and that said Letters Patent are hereby corrected as shown below:

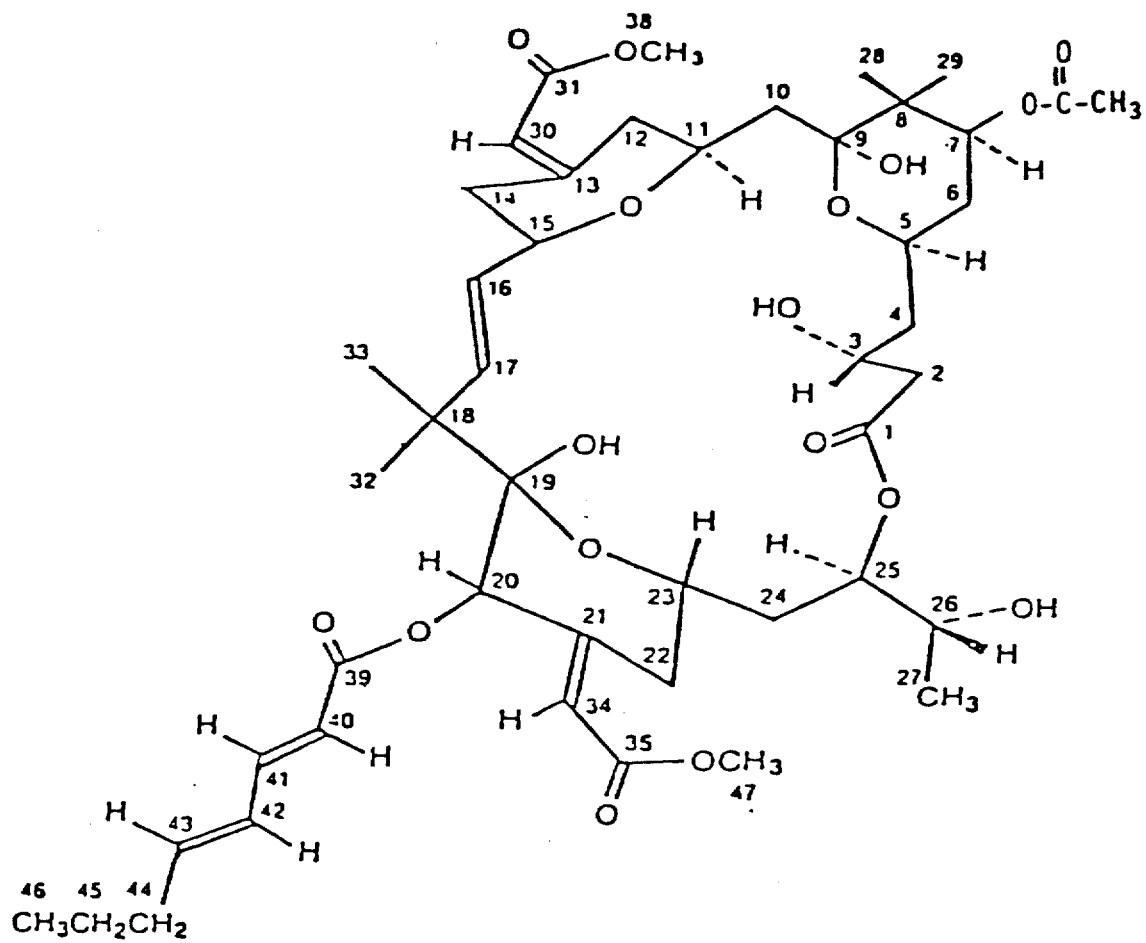

Bryostatin 1

UNITED STATES PATENT AND TRADEMARK OFFICE
CERTIFICATE OF CORRECTION

PATENT NO. : 4,560,774

DATED : 24 December 1985

INVENTOR(S) : G.R. Pettit, et al.

It is certified that error appears in the above-identified patent and that said Letters Patent is hereby corrected as shown below:

Column 18, Chart II should appear as follows:

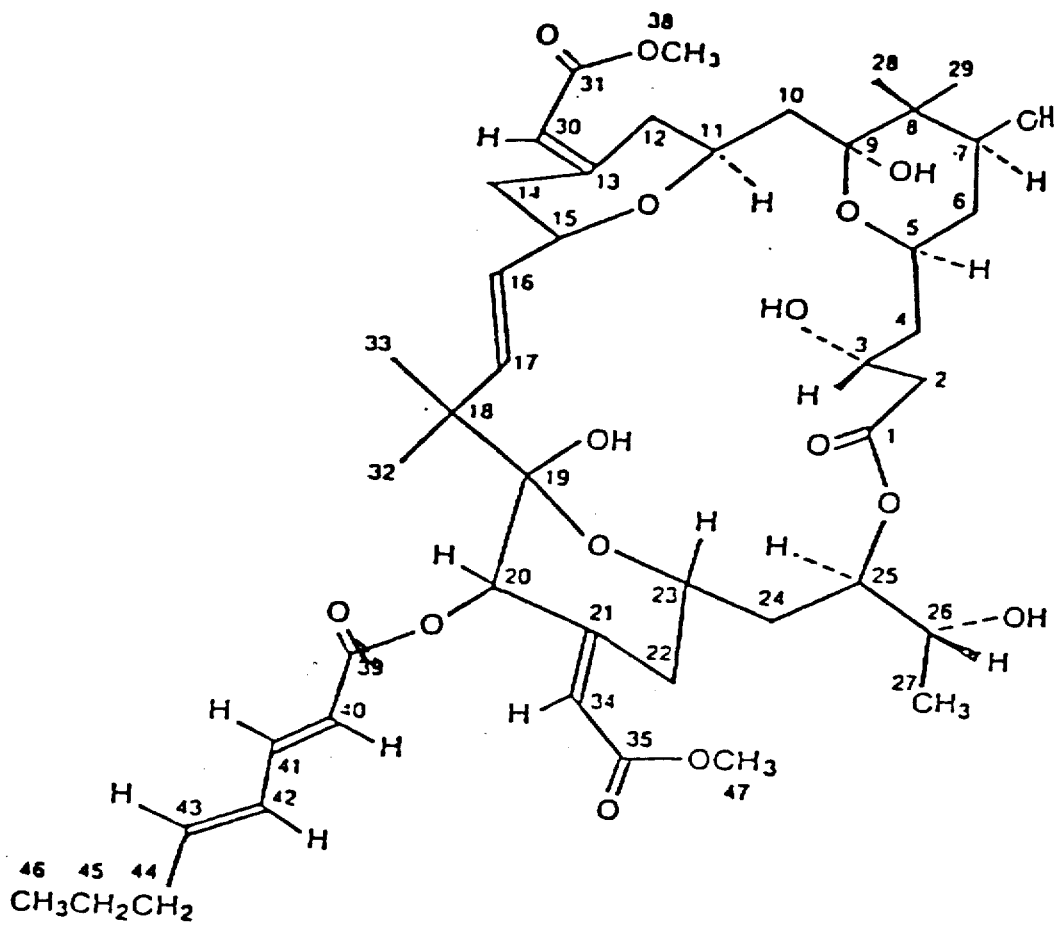

Bryostatin 2

UNITED STATES PATENT AND TRADEMARK OFFICE
CERTIFICATE OF CORRECTION

PATENT NO. : 4,560,774        Page 4 of 8
DATED     : 24 December 1985
INVENTOR(S) : G.R. Pettit, et al.

It is certified that error appears in the above-identified patent and that said Letters Patent is hereby corrected as shown below:

Column 19, Chart III should appear as follows:

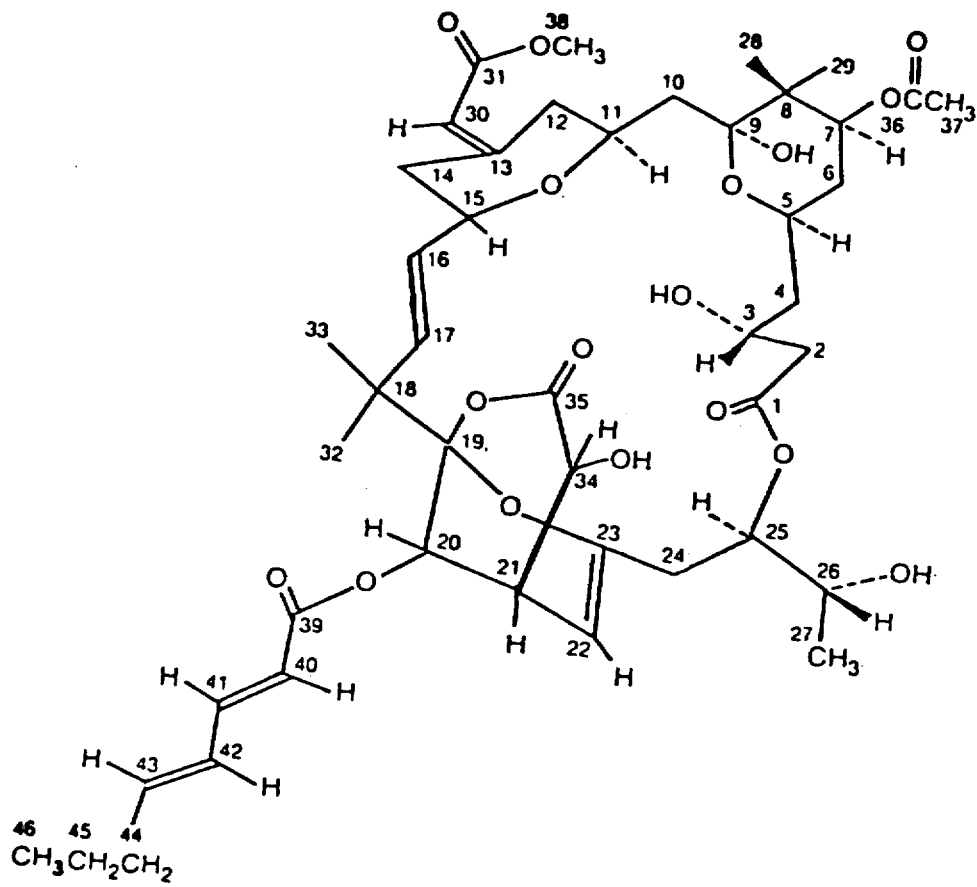

Bryostatin 3

UNITED STATES PATENT OFFICE
CERTIFICATE OF CORRECTION

Patent No. 4,560,774          Dated 24 December 1985

Inventor(s) G.R. Pettit, et al

It is certified that error appears in the above-identified patent and that said Letters Patent are hereby corrected as shown below:

Column 20, Chart IV should appear as follows:

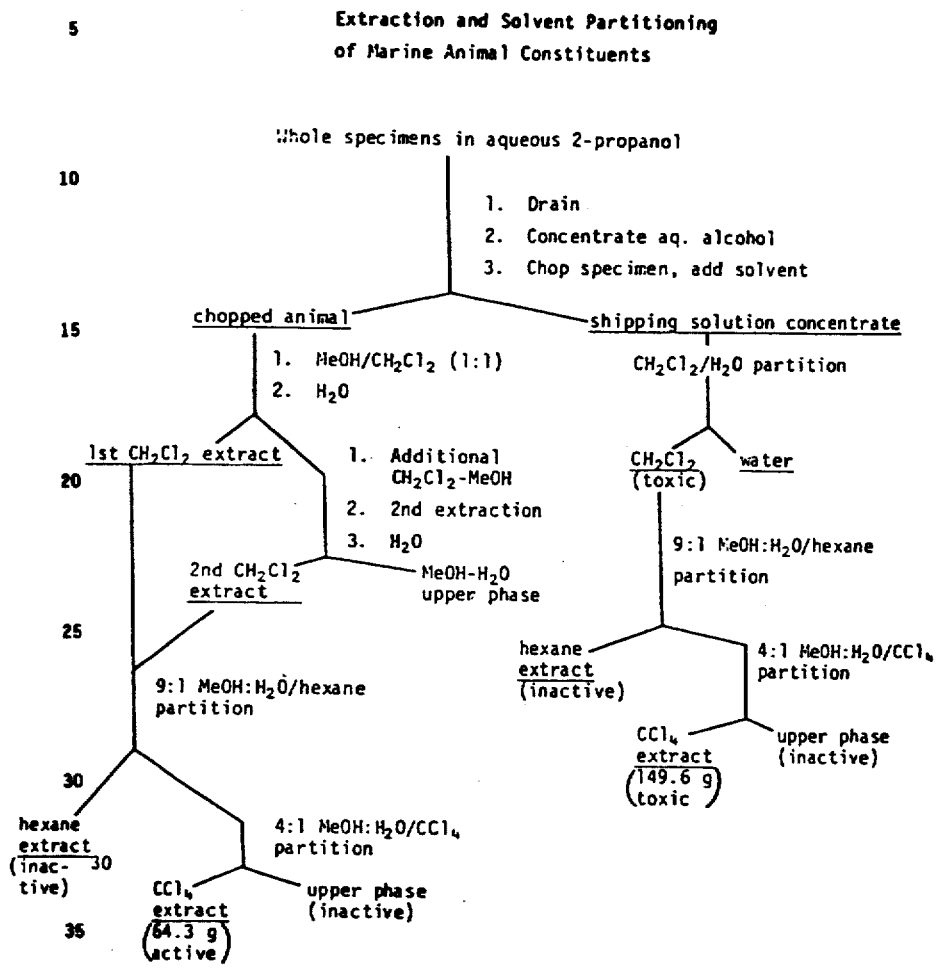

UNITED STATES PATENT OFFICE
CERTIFICATE OF CORRECTION

Page 6 of 8

Patent No. 4,560,774           Dated 24 December 1985

Inventor(s) G.R. Pettit, et al.

It is certified that error appears in the above-identified patent and that said Letters Patent are hereby corrected as shown below:

Columns 21-22, the formula should appear as follows:

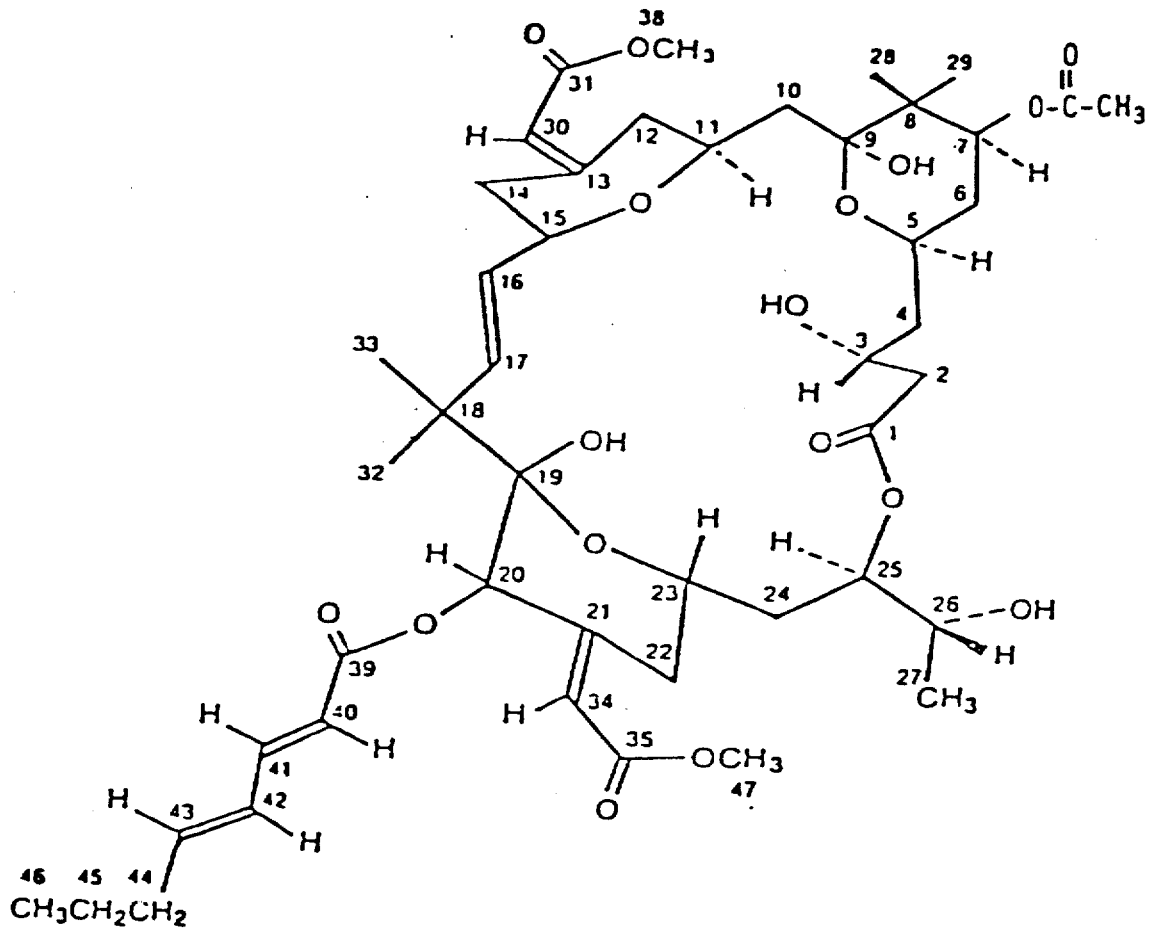

UNITED STATES PATENT OFFICE
CERTIFICATE OF CORRECTION

Patent No. 4,560,774  Dated 24 December 1985

Inventor(s)  G.R. Pettit, et al.

It is certified that error appears in the above-identified patent and that said Letters Patent are hereby corrected as shown below:

Column 22, the formula should appear as follows:

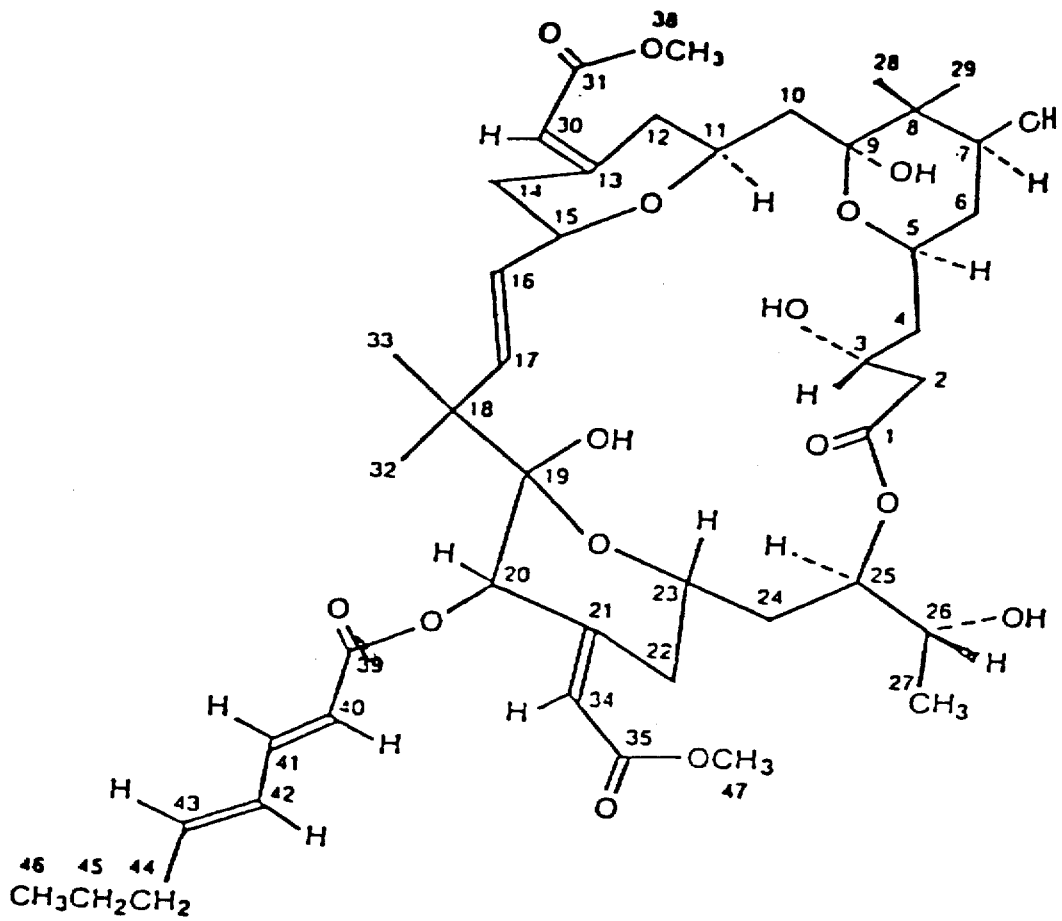

UNITED STATES PATENT OFFICE
CERTIFICATE OF CORRECTION

Patent No. 4,560,774      Dated 24 December 1985

Inventor(s) G.R. Pettit, et al.

It is certified that error appears in the above-identified patent and that said Letters Patent are hereby corrected as shown below:

Column 24, the formula should appear as follows: